(12) United States Patent
Yannopoulos et al.

(10) Patent No.: US 12,138,374 B2
(45) Date of Patent: Nov. 12, 2024

(54) DEVICES AND METHODS TO INFUSE GASES INTO AND OUT OF BLOOD

(71) Applicants: Demetris Yannopoulos, Edina, MN (US); Robert F. Wilson, Roseville, MN (US)

(72) Inventors: Demetris Yannopoulos, Edina, MN (US); Robert F. Wilson, Roseville, MN (US)

( * ) Notice: Subject to any disclaimer, the term of this patent is extended or adjusted under 35 U.S.C. 154(b) by 970 days.

(21) Appl. No.: 16/978,677

(22) PCT Filed: Mar. 5, 2019

(86) PCT No.: PCT/US2019/020819
§ 371 (c)(1),
(2) Date: Sep. 4, 2020

(87) PCT Pub. No.: WO2019/173387
PCT Pub. Date: Sep. 12, 2019

(65) Prior Publication Data
US 2020/0397968 A1    Dec. 24, 2020

Related U.S. Application Data

(60) Provisional application No. 62/638,661, filed on Mar. 5, 2018.

(51) Int. Cl.
*A61M 1/32* (2006.01)
*A61K 33/00* (2006.01)
(Continued)

(52) U.S. Cl.
CPC ............... *A61M 1/32* (2013.01); *A61K 33/00* (2013.01); *A61M 1/1698* (2013.01); *A61M 1/285* (2013.01); *A61M 1/3626* (2013.01); *B01F 23/231* (2022.01); *B01F 23/2375* (2022.01); *B01F 23/237612* (2022.01); *B01F 23/238* (2022.01); *B01F 31/28* (2022.01); *B01F 31/80* (2022.01); *B01F 31/85* (2022.01);
(Continued)

(58) Field of Classification Search
CPC ...... A61M 1/1698; A61M 1/285; A61M 1/32; A61M 1/3626; A61M 2202/0007; A61M 2202/0014; A61M 2202/0208; A61M 2202/0225; A61M 2202/0413; B01F 23/231; B01F 23/2375; B01F 23/237612; B01F 23/238; B01F 31/85; B01F 31/28; B01F 31/80; A61K 33/00
See application file for complete search history.

(56) References Cited

U.S. PATENT DOCUMENTS

2006/0273695 A1   12/2006  Savage
2010/0228122 A1    9/2010  Keenan et al.
(Continued)

OTHER PUBLICATIONS

WIPO, U.S. International Search Authority, International Search Report and Written Opinion mailed Jun. 28, 2019 in International Patent Application No. PCT/US2019/020819, 11 pages.

*Primary Examiner* — John Kim
(74) *Attorney, Agent, or Firm* — Inskeep IP Group, Inc.

(57) ABSTRACT

Gaseous nanobubbles are created and infused into the blood stream to therapeutic effect such as oxygenation. The nanobubbles may be created inside or outside of the patient, either during infusion or prior to infusion. CO2 is extracted from the blood to improve oxygen.

11 Claims, 11 Drawing Sheets

(51) Int. Cl.
A61M 1/16 (2006.01)
A61M 1/28 (2006.01)
A61M 1/36 (2006.01)
B01F 23/23 (2022.01)
B01F 23/231 (2022.01)
B01F 23/237 (2022.01)
B01F 23/2375 (2022.01)
B01F 31/20 (2022.01)
B01F 31/80 (2022.01)
B01F 31/85 (2022.01)

(52) U.S. Cl.
CPC ............... *A61M 2202/0007* (2013.01); *A61M 2202/0014* (2013.01); *A61M 2202/0208* (2013.01); *A61M 2202/0225* (2013.01); *A61M 2202/0413* (2013.01)

(56) References Cited

U.S. PATENT DOCUMENTS

| | | |
|---|---|---|
| 2011/0270156 A1 | 11/2011 | Hassan et al. |
| 2013/0207285 A1 | 8/2013 | Cooke |
| 2014/0010848 A1 | 1/2014 | Kheir et al. |
| 2015/0164787 A1 | 6/2015 | Kheir et al. |
| 2021/0007759 A1* | 1/2021 | Jiang ..................... A61B 18/26 |

* cited by examiner

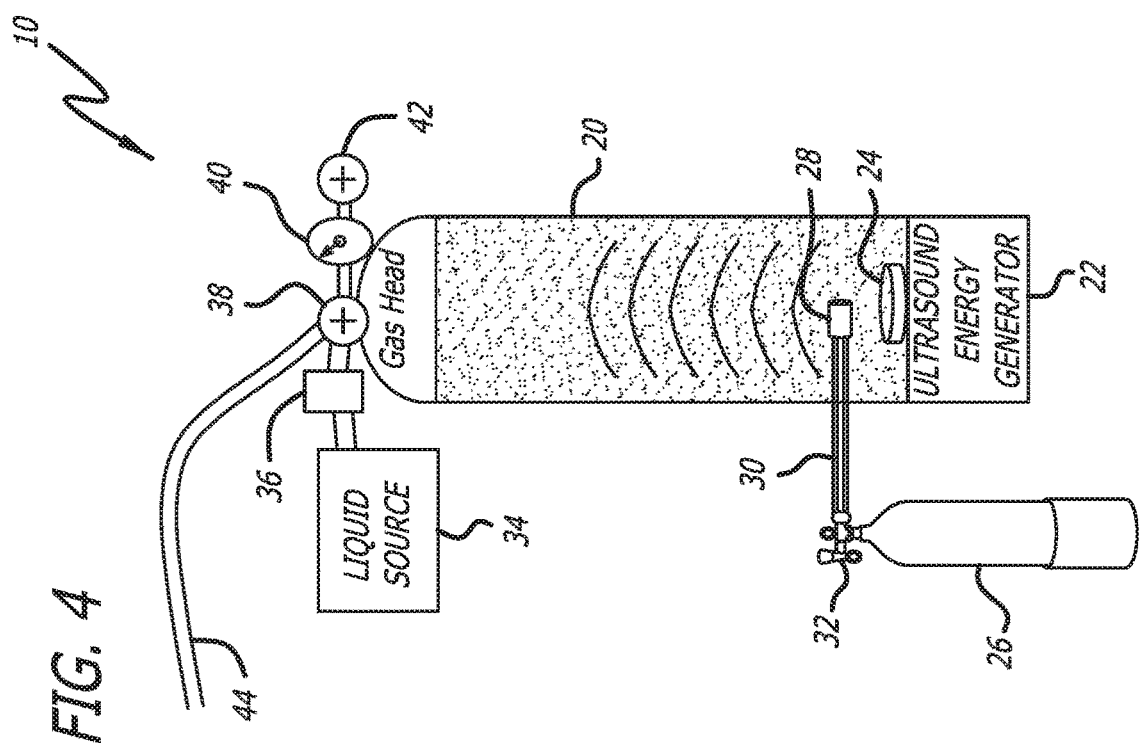
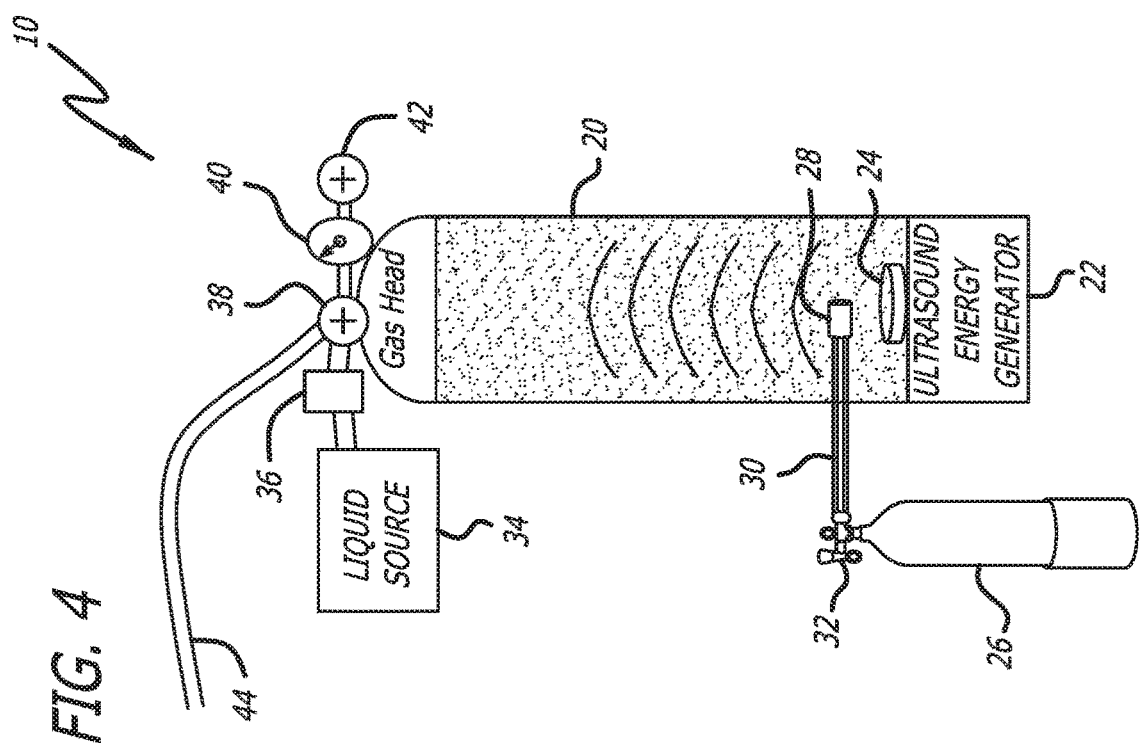

DEVICES AND METHODS TO INFUSE GASES INTO AND OUT OF BLOOD

RELATED APPLICATIONS

This application is the U.S. National Phase of and claims priority to International Patent Application No. PCT/US2019/020819, International Filing Date Mar. 5, 2019, entitled Devices And Methods To Infuse Gases Into And Out Of Blood; which claims benefit of U.S. Provisional Application Ser. No. 62/638,661 filed Mar. 5, 2018 entitled Devices And Methods To Infuse Gases Into And Out Of Blood; both of which are incorporated herein by reference in their entireties.

FIELD OF THE INVENTION

The invention described here is a method for oxygenating blood by injection of nanobubble saturated fluid into the body or by creation of nano-bubbles within the body, through a catheter system placed into the body or as part of a catheter system that draws blood from the body, oxygenates the blood outside the body and then returns the blood to the body. In addition, a method for removing $CO_2$ is described.

BACKGROUND OF THE INVENTION

The creation of nanobubbles has previously been shown to occur when oxygen or other gases are infused into a liquid though a diffusion apparatus, such as a small-pore ceramic stone. Ultrasonication of the oxygen-infused solution then breaks apart the gas bubbles in the liquid, creating gas particles having diameters measured in nanometers. This process can be performed in a beaker, but its application to blood and, in particular, a stream of rapidly flowing blood, has prevented the use of nanobubble oxygen therapy to humans.

Mammalian blood is composed of cellular components, such as red and white blood cells, and platelets, and plasma consisting of proteins, electrolytes, water, other molecules and dissolved gases. As the blood passes through the lungs, oxygen from the lung alveolus ($pO_2$ approximately 100 mmHg) diffuses across the alveolar membrane to the venous blood ($pO_2$ typically ~40 mmHg at the pulmonary arterioles). Over the period of red cell transit through the exchange zone, oxygen diffusion equilibrates the partial pressure of the blood ($PaO_2$) maximally saturating hemoglobin and the partial pressure of the arterial blood, producing a $PaO_2$ of 100 mmHg in the blood as well. The greater the $pO_2$ gradient from the alveolar air to the blood plasma, the greater the oxygen diffusion rate and oxygen load of the circulating blood. Oxygen from the plasma rapidly equilibrates with the $pO_2$ inside red blood cells, where the oxygen is absorbed by the hemoglobin molecules in red blood cells. A means to continuously load the plasma with diffused oxygen, which could then absorbed by hemoglobin, would facilitate transfer of oxygen to the blood and therefore to the body as the blood circulates.

The problem with simple infusion of gaseous oxygen into the blood is that the oxygen bubbles will coalesce to form large air bubbles. As the air bubbles approach the microcirculatory vessels (e.g. <1 mm diameter), the surface tension of the bubbles prevents passage of the bubbles though the circulation, creating an obstruction that stops blood flow. When a sufficient quantity of gas is injected into the venous system, the injected gas will result in circulatory collapse due to obstruction of blood passing through the lung. In the arterial system, gas injections of 1 ml or less can result in local tissue ischemia. Additionally, the diffusion of gasses from the larger bubbles to the plasma is relatively slow. Since the blood volume of mammals is typically recirculated through the entire body in about one minute, the gas from large bubbles is not absorbed in one circulation time and the bubbles remain in solution, obstructing the microcirculation.

The microcirculation can pass particles >15 μm diameter, but air bubbles in the micrometer size typically coalesce in the blood and subsequently cause obstruction. Gas bubbles under 200 nm diameter, however, behave differently. These nanobubbles have significant surface energy and stay in solution until the gas diffuses into the surrounding solution. Nanometer particles easily pass through the circulation and do not coalesce. In addition, they do not rise against gravity and their motion is determined closely by the Brownian model of random motion. In addition, microbubbles can remain in solution for days. Therefore, loading a blood solution with nanometer diameter oxygen bubbles is a method to transfer oxygen into the blood without causing obstruction to blood passage through the microcirculation while the gas from the bubbles diffuses into the plasma.

The problem with application of this principle to living organisms is the difficulties presented by the creation of nanometer size bubbles in vivo, the mixing of the nanobubbles into a rapidly flowing blood stream, and preventing aggregation of the bubbles over time due to interactions with plasma proteins and electrolytes that alter surface energy of the bubble. In addition, initiation of thrombosis through platelet and clotting factor activation as a result of the agitation of bubbles in a mixing chamber might limit the ability to infuse and mix blood and gaseous oxygen.

OBJECTS AND SUMMARY OF THE INVENTION

Embodiments of oxygenation systems are presented herein that address the aforementioned difficulties and provide solutions that allow the exploitation of the advantages presented by nanobubbles. An oxygenation system of the present invention has three main components: an infusion apparatus to infuse oxygen into the blood, a means of creating nanobubbles that are less than one micrometer in diameter (nanobubbles), and a mixing apparatus to ensure that the infused nanobubbles are mixed with the blood. The method for removing $CO_2$ can be used alone or in conjunction with the method for continuous oxygen infusion.

In an additional embodiment, additional device is used to cause rupture or leakage of gas from nanobubbles. The use of ultrasound to rupture gas-containing lipid microbubbles has been described and is used to rupture ultrasound contrast agent microbubbles. Similarly, ultrasound rupture of drug containing lipid shell microbubbles has been described. Other shells around microbubbles or nanobubbles have also been described.

Nanobubbles described herein do not have a shell. Rather, the fluid gas interface has substantial surface tension and surface energy caused in part by electrostatic forces. As a result, the gas pressure inside the nanobubble exceeds atmospheric pressure. Ultrasound energy, particularly at the resonant frequency of the bubble, can disrupt the surface attraction, leading to bubble rupture or leakage of gas into the surrounding fluid. The specific ultrasound frequencies and power depend on the nanobubble size, the fluid properties, the gas within the nanobubble, and the composition and thickness of the medium transmitting the ultrasound.

There are many applications of this ultrasound-induced rupture. Release oxygen or other gases into the blood stream once the nanobubble containing fluid, typically saline, is in the blood vessel facilitates rapid oxygenation or gas release. In many preparations, nanobubbles can stay in solution for days to a month. Effective oxygenation of oxygen nanobubbles would be facilitated by ultrasound induced nanobubble rupture. An additional application of ultrasound induced rupture is the ability to selectively oxygenate or deliver gas to a particular organ. Application of ultrasound to the organ or it's blood supply causes the gas concentration in the plasma, interstitial fluid, or cell (for nanobubbles that enter the cell) to rise.

It is recognized that there may be other methods to cause nanobubble rupture. For example, magnetic or ferro magnetic gas within a nanobubble would heat under the appropriate alternating magnetic field. The increased energy of the gas would then cause increased pressure, leading to nanobubble or microbubble rupture. In one embodiment, the gas within the bubble can be only partially composed of a magnetically susceptible gas. The embodiment is particularly useful for infusion of non-magnetically susceptible gas or gases with local therapeutic benefit.

One aspect of the invention provides a method of infusing blood with a gas that involves creating bubbles of gas in a medium; reducing said bubbles to nanobubbles, said nanobubbles having diameters of less than 500 nm; introducing said medium containing said nanobubbles into a bloodstream of a patient; and rupturing said nanobubbles using external energy at a target location.

The gas bubbles may be oxygen, and they may be created in vivo or outside of the patient.

In one embodiment, rupturing the nanobubbles is accomplished by energizing the nanobubbles using ultrasonic energy at a resonant frequency of the nanobubbles.

One aspect includes reducing the bubbles to nanobubbles by ensonifying said bubbles. Ensonifying may be done using ultrasound.

In one aspect, creating bubbles of gas in a medium comprises creating bubbles of gas in blood from said bloodstream that has been routed into a catheter.

In another aspect, introducing said medium into the bloodstream of the patient comprises releasing said blood that has been routed into the catheter back into the bloodstream through blood outflow holes created in the catheter.

Another aspect of the invention provides a system for infusing blood with a gas that includes: a gas source; a liquid medium; a gas infuser connected to said gas source and located in said liquid medium that creates gas bubbles when gas from said gas source flows through said gas diffuser; an ensonifier located in said liquid medium and connected to a power source wherein when energized said ensonifier reduces said gas bubbles to nanobubbles, said nanobubbles having a diameter of less than 500 nm; and a catheter useable to deliver said nanobubbles in said medium to a bloodstream of a patient.

One aspect provides a gas source that is an oxygen source.
Another aspect provides a liquid medium that is saline.
Another aspect provides a liquid medium that is blood.
Yet another aspect provides a gas diffuser that is a ceramic stone.

Still another aspect includes an ensonifier that is a piezoelectric ultrasound transducer.

Yet another aspect includes an ensonifier that is an ultrasound generator attached to a wire.

The ensonifier may be located within said catheter.

One aspect of the invention involves a system for removing $CO_2$ from a bloodstream comprising: a first chamber useable to receive blood from a patient; a second chamber; a permeable membrane separating said first chamber from said second chamber; a vacuum useable to lower a pressure in said second chamber such that flow of $CO_2$ from said blood through said membrane is increased; and a flow pump connected to said first chamber on an input side of said flow pump and connected to said patient on an output side of said flow pump such that when energized, said flow pump delivers blood from said first chamber to said patient.

One aspect of the invention further includes a system for infusing blood with a gas connected between said first chamber and said flow pump.

Another aspect of the invention provides a system for infusing blood with a gas connected to said output side of said flow pump.

In one aspect of the invention, the system also includes a sonification system connected between said first chamber and said flow pump to prevent gas bubble coalescence and to reduce a diameter of any bubbles present in the blood to less than 10 micrometers.

In another aspect of the invention, the system also includes a $CO_2$ infusion controller that controls the pressure in said second chamber.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 3 is a schematic of the system of FIG. 1 filled with saline and oxygen bubbles;

FIG. 4 is a schematic of the system of FIG. 3 showing the oxygen bubbles converted to nanobubbles;

DESCRIPTION OF EMBODIMENTS

Figure 1:
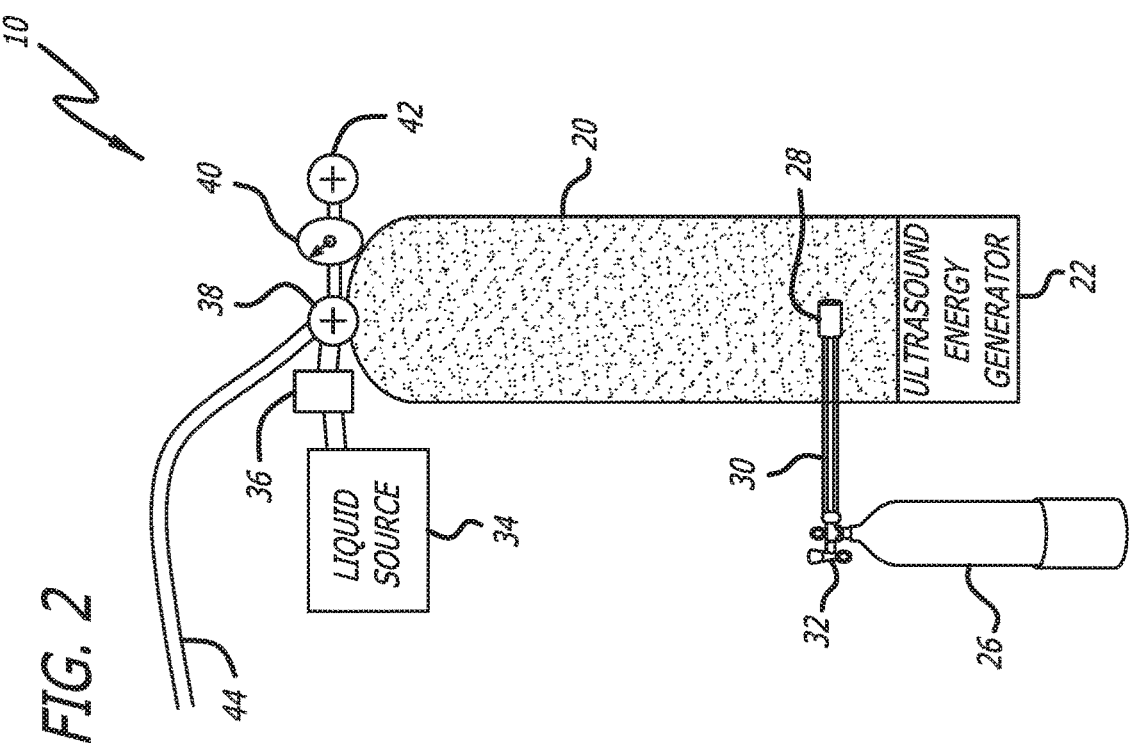
FIG. 1 is a schematic of an embodiment of an oxygenation system of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

FIGS. 1-5 show an embodiment 10 of an oxygenation system, which represents a rapid infusion embodiment of the invention. In the rapid infusion embodiment 10 of the invention, gaseous oxygen is dissolved under pressure into a physiologic solution consisting of water and other dissolved components, such as salts, acids and bases (for example, physiologic saline with 0.9% NaCl by weight). The amount of oxygen that can be dissolved has been previously measured and varies with the pressure and temperature of the fluid and the ionic constituents of the fluid. It is estimated that the pressure of the oxygen-infused solution would be held at pressure greater than atmospheric pressure in 0.9% NaCl water, or enough to provide several minutes of oxygen consumption for a typical 70 kg adult.

Embodiment 10 utilizes a tank 20 to prepare and store a nanobubble solution. The tank 20 contains within it an ultrasound energy generator 22. The ultrasound energy generator may utilize a piezoelectric ultrasound transducer 24. The system 10 also includes an oxygen source 26, such as an oxygen canister, connected to the tank 20 with oxygen supply tubing 30 via an oxygen supply valve 32. The oxygen tubing 30 passes into the tank 20 and terminates with an infusion gas diffuser 28. As used herein the term "infuser" refers to anything that introduces a gas into a liquid medium. A simple tube could thus be an infuser. A "diffuser", as used herein, refers to a device attached to an infuser that reduces the size of the bubbles being introduced.

Also connected to the tank 20 is a liquid source 34. The liquid source 34 is shown as being connected to the tank 20 with a connector 36 and a three-way flow valve 38. In addition to the liquid source 34, the three-way flow valve 38 is also connected to a pressure gauge 40, which is further connected to a vent and fill valve 42. The third connection to the three-way flow valve 38 is patient tube 44.

Figure 2:
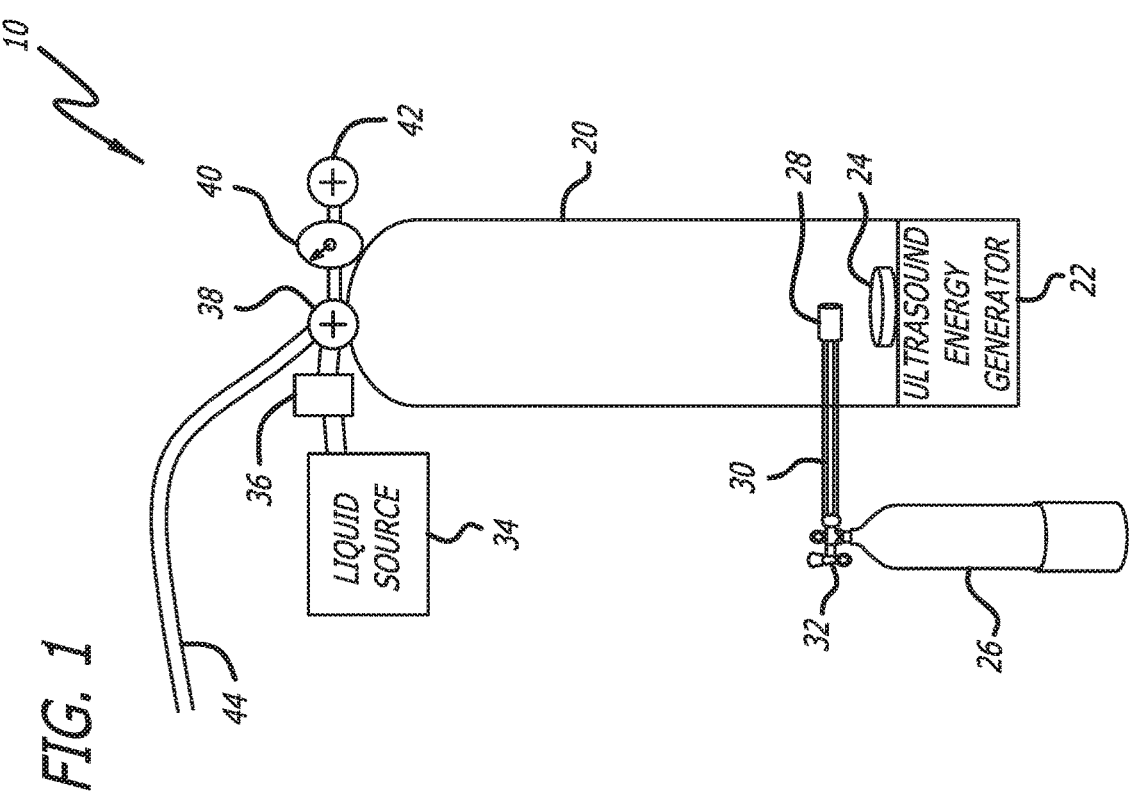
FIG. 2 is a schematic of the system of FIG. 1 filled with saline.

In FIG. 1, the system 10 is empty but configured for preparing the nanometer diameter oxygen saturated solution. Valve 32 is closed, preventing oxygen from canister 26 from entering the tank 20. The piezoelectric ultrasound transducer 22 is not active. The three-way flow valve 38 is then positioned to allow liquid from source 34 to flow into the tank 20. As the tank 20 is filled, the vent valve 42 is opened to allow gas to escape from the tank 20, making room for the liquid. FIG. 2 shows the tank 20 full.

Once the tank 20 is full, oxygen is introduced into the tank 20, as shown in FIG. 3. The three-way valve 38 is turned to the pressure gauge position such that pressure gauge 40 may be monitored. Oxygen valve 32 is opened, allowing oxygen from the canister 26 to enter the tank 20 through the tubing 30 and the diffuser 28. When the oxygen is infused through the diffuser 28, the diffuser 28 creates small bubbles in the 0.5-2 mm diameter range. Alternatively, a ceramic stone or other apparatus is used to produce very small air bubbles (less than 1 mm diameter and preferably in the range of 1-50 μm).

The tank 20 is ensonified at about 20-60 kHz frequency sound, although other frequencies could be used. The ultrasound will result in 200-500 nanometer diameter bubbles (or less) and supersaturation of the gas with oxygen. The pressure vessel is then vented by injecting saline solution and expelling the gas head, such that the remaining gas head is minimized. The pressure vessel is then stored for future use. A storage container that periodically ensonifies the pressure chamber to keep the dissolved gas bubbles in the nanometer size range facilitates storage.

When a desired ensonification pressure is reached, as indicated on pressure gauge 40, ensonification can begin using the configuration shown in FIG. 4. The oxygen valve 32 is closed and the piezoelectric transducer 24 is energized to vibrate at a high frequency, for example, in the range of 20-60 kHz, more preferably between 40 and 50 kHz. Good results have been obtained at 44 kHz.

Figure 5:
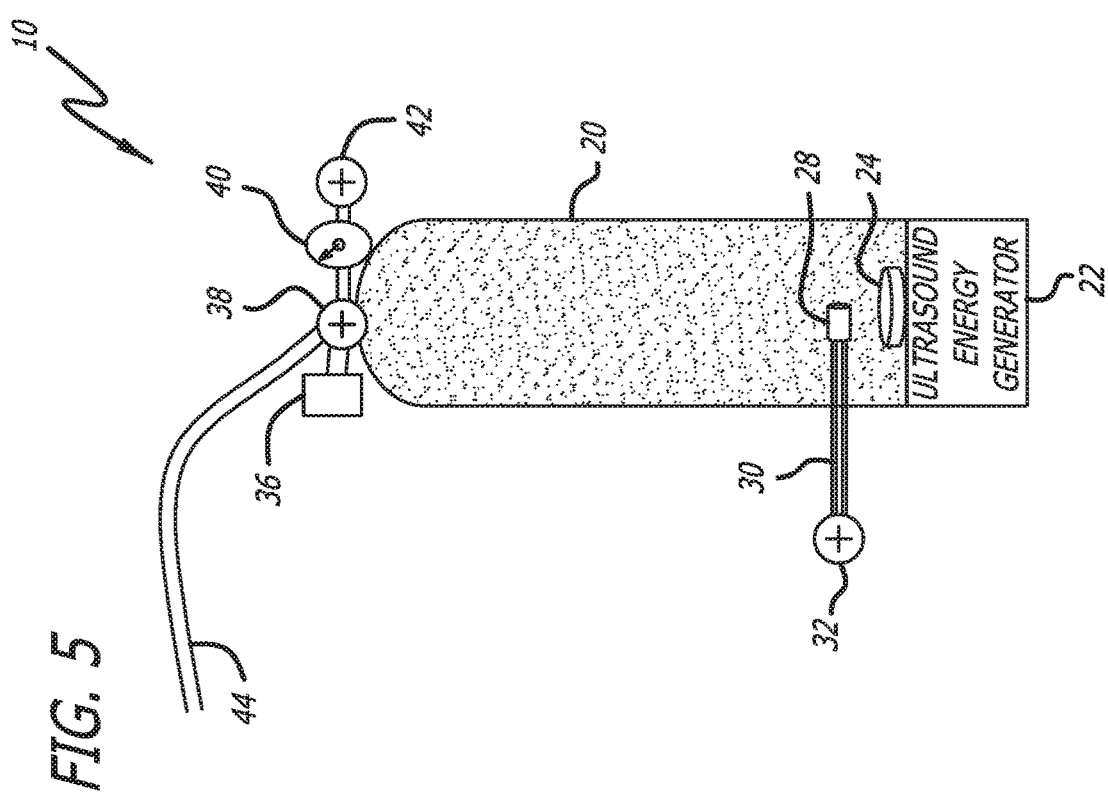
FIG. 5 is a schematic of the system of FIG. 4 during a venting procedure.
Figure 6:
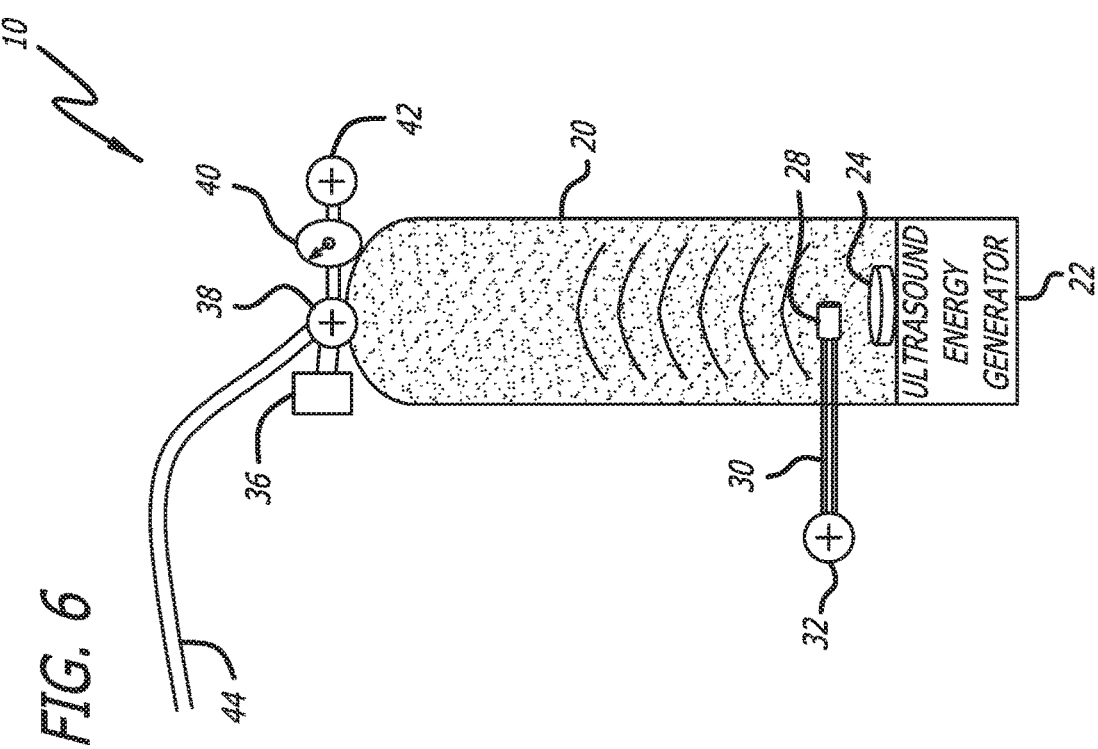
FIG. 6 is a schematic of the system of FIG. 5 being re-ensonified.

After ensonification is complete, the tank 20 is vented, as shown in FIG. 5, in the event that the pressure in the tank 20 is too high, such as above 1 bar. Venting is accomplished by opening the vent valve 42 while monitoring the pressure gauge 40. Once the pressure is at an acceptable level, the vent valve 42 is closed and re-ensonification of the liquid may be accomplished by re-energizing the piezoelectric transducer, as shown in FIG. 6.

Figure 7:
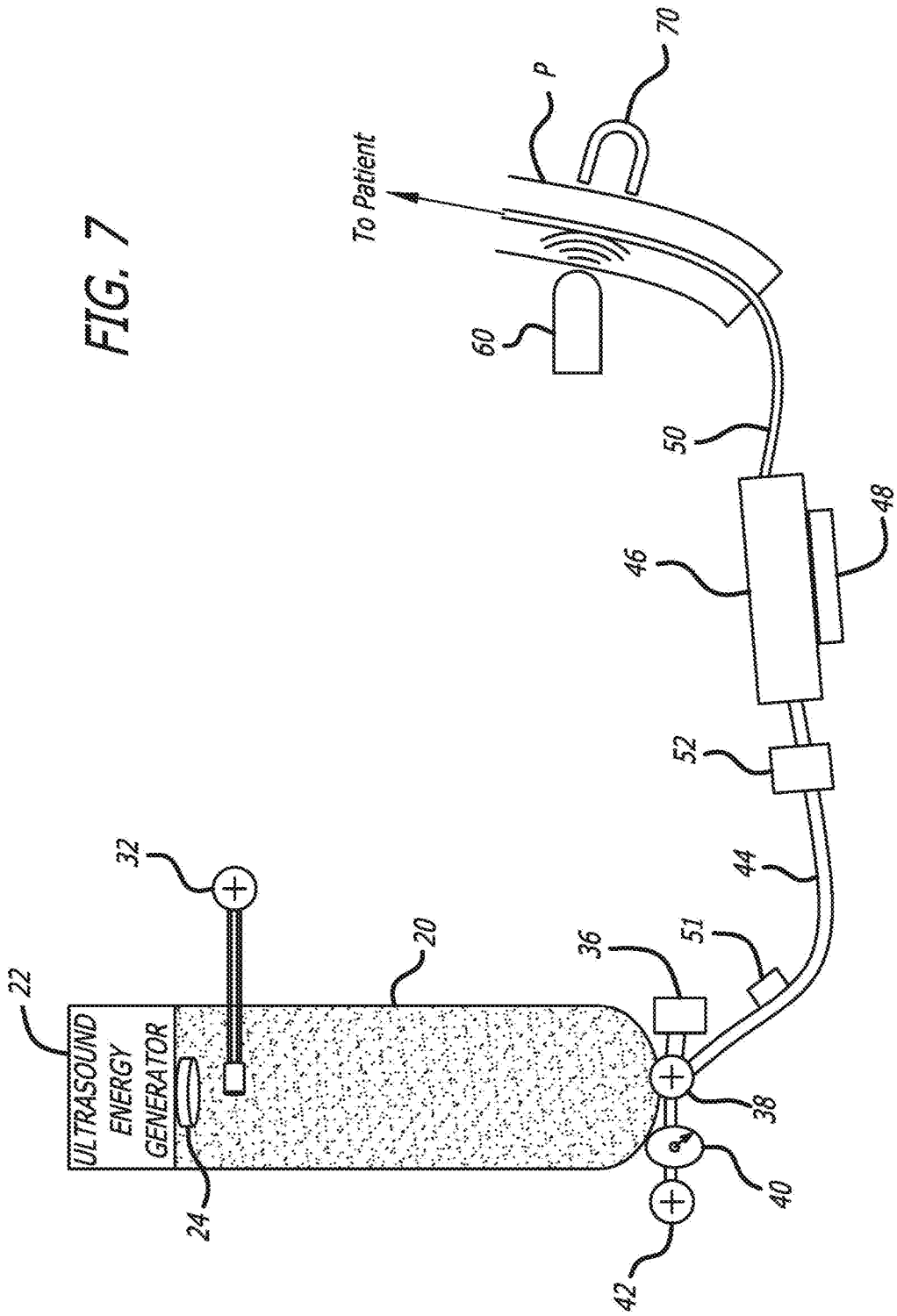
FIG. 7 is a schematic of the system of FIG. 6 inverted and ready to pump fluid to a patient.

Having completed the ensonification process, the liquid may be administered to a patient. Referring to FIG. 7, the tank 20 is first inverted to avoid the infusion of any air head that may be present into the patient. The oxygen canister may be removed and the tubing 30 and valve 32 may be opened for venting the tank 20.

The three-way valve is turned to direct flow from the tank 20 to the tubing 44, which has been attached to a pump 46 having a pump controller 48. The pump is connected to a catheter 50 that has been connected to the patient P after purging, either intravenously or intraosseously. Infusion may then begin by activating the pump 46 via the controller 48. In one embodiment, a macro air detector 52 is connected to the tubing 44 and shuts off the pump if a macro bubble (>1 mm diameter) is detected. It is envisioned that the pump may be unnecessary in some cases and that the tank 20 may simply be elevated to provide head pressure.

Figure 9:
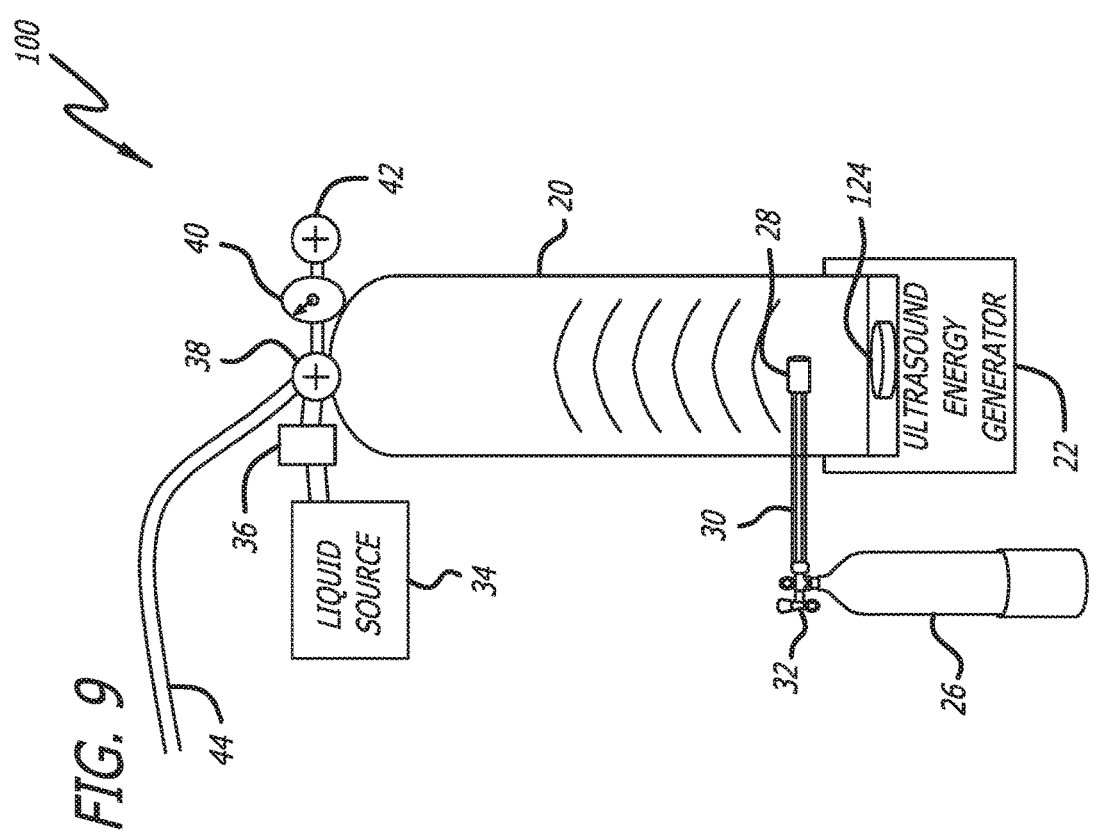
FIG. 9 is a schematic of the system of FIG. 8 in a connected configuration.
Figure 8:
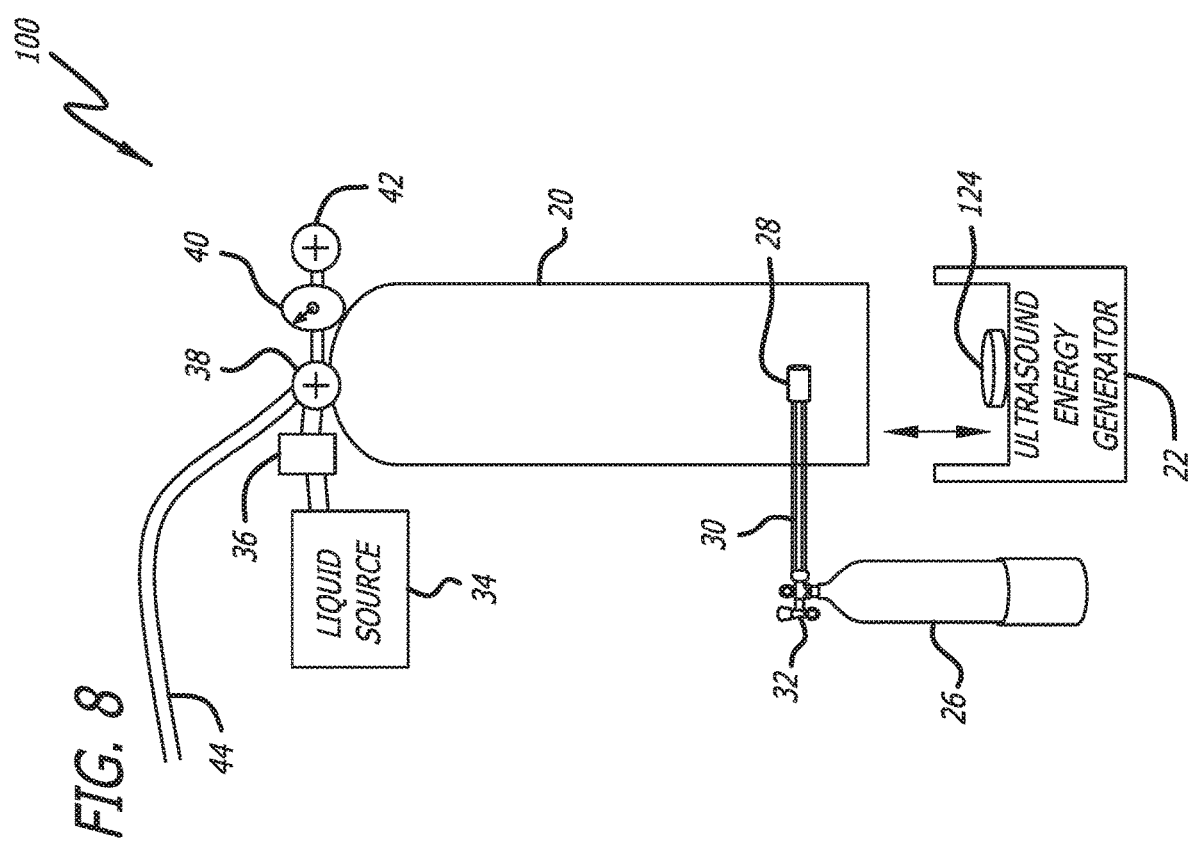
FIG. 8 is a schematic of an embodiment of an oxygenation system of the invention.

FIGS. 8 and 9 show an alternate embodiment 100 of an oxygenation system of the invention. The embodiment 100 of FIGS. 8 and 9 differs from embodiment 10 only in that embodiment 100 has a piezoelectric transducer 124 that is located outside of the tank 20, between the tank 20 and the ultrasound energy generator 22. This configuration may allow tanks to be used for storage and re-ensonification more easily.

Referring back to FIG. 7, the fluid is transferred to the patient by first inverting the pressurized tank 20 such that the fluid leaves the bottom of the pressure container and the gas remains at the top. A regulator controlling the rate of flow out of the pressure container into the patient is opened to permit flow of the nanobubble infused fluid. In one embodiment, the gas source 26 is removed and the valve 32 is used as a regulator. An ultrasonic apparatus 51 ensonifies the fluid as it leaves the tank to ensure that pressurized bubbles that have expanded in exposure to atmospheric pressure are returned to nanometer diameters bubbles. The fluid is rapidly infused into the vein, whereupon the nanobubbles of oxygen diffuse large quantities of oxygen to the blood plasma and subsequently to the hemoglobin. The preferred method for sonification is a piezo-electric crystal bonded or attached to the outflow tubing or to a chamber within the path between the pressure vessel and the patient. Alternatively, an ultrasound generator can be attached to a wire or other conductor of ultrasound. The wire or other conductor is then attached to the flow of fluid, directing in the fluid path or about the tubing that contains the fluid. High frequency mechanical vibrational waves may also be used to maintain the nanobubbles consistency Once the nanobubble solution, either oxygenated or filled with another gas, is introduced into the bloodstream, the nanobubbles may be ruptured allowing the gas within the nanobubbles to be released. As mentioned previously, the nanobubbles described herein do not have a shell. As such, once the nanobubbles are ruptured and the gas is dissolved, no shell remnants remain. Rather than having a shell, the fluid gas interface has substantial surface tension and surface energy caused in part by electrostatic forces. As a result, the gas pressure inside the nanobubble exceeds atmospheric pressure. Ultrasound energy, particularly at the resonant frequency of the bubble, can disrupt the surface attraction, leading to bubble rupture or leakage of gas into the surrounding fluid. The specific ultrasound frequencies and power depend on the nanobubble size, the fluid properties, the gas within the nanobubble, and the composition and thickness of the medium transmitting the ultrasound.

There are many applications of this ultrasound-induced rupture. Release oxygen or other gases into the blood stream once the nanobubble containing fluid, typically saline, is in the blood vessel facilitates rapid oxygenation or gas release. In many preparations, nanobubbles can stay in solution for days to a month. Effective oxygenation of oxygen nanobubbles would be facilitated by ultrasound induced nanobubble rupture. An additional application of ultrasound induced rupture is the ability to selectively oxygenate or deliver gas to a particular organ. Application of ultrasound to the organ or it's blood supply causes the gas concentration in the plasma, interstitial fluid, or cell (for nanobubbles that enter the cell) to rise.

FIG. 7 shows an ultrasound emitter 60 being placed at a site on the patient P where the delivery of the gas is desired. The emitter 60 is energized and tuned to the resonant frequency of the bubbles. The ultrasonic energy from the emitter 60 harmlessly penetrates the patient and ruptures the bubbles.

It is recognized that there may be other methods to cause nanobubble rupture. For example, magnetic or ferro magnetic gas within a nanobubble would heat under the appropriate alternating magnetic field. Thus a magnetic field generator 70 may be used to increase the energy of the gas that would then cause increased pressure, leading to nanobubble or microbubble rupture. In one embodiment, the gas within the bubble can be only partially composed of a magnetically susceptible gas. The embodiment is particularly useful for infusion of non-magnetically susceptible gas or gases with local therapeutic benefit.

Figure 10:
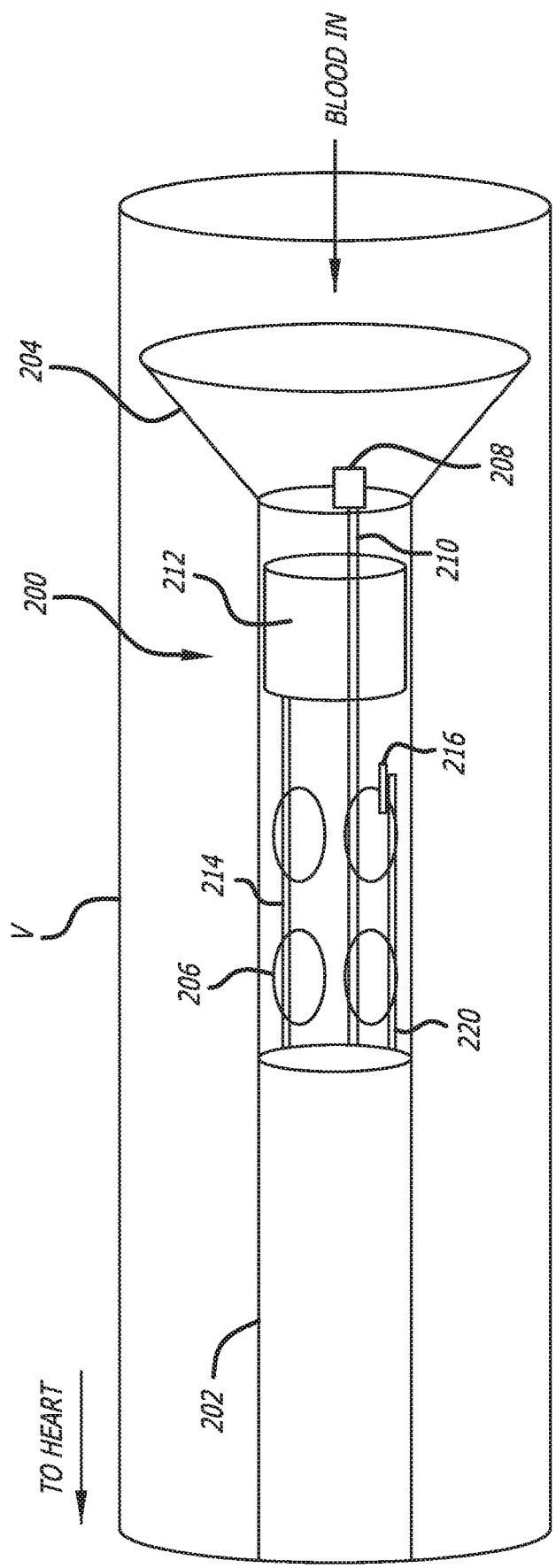
FIG. 10 is an elevation view of an embodiment of distal end of an oxygen infusion catheter system of the invention inside a vein.
Figure 11:
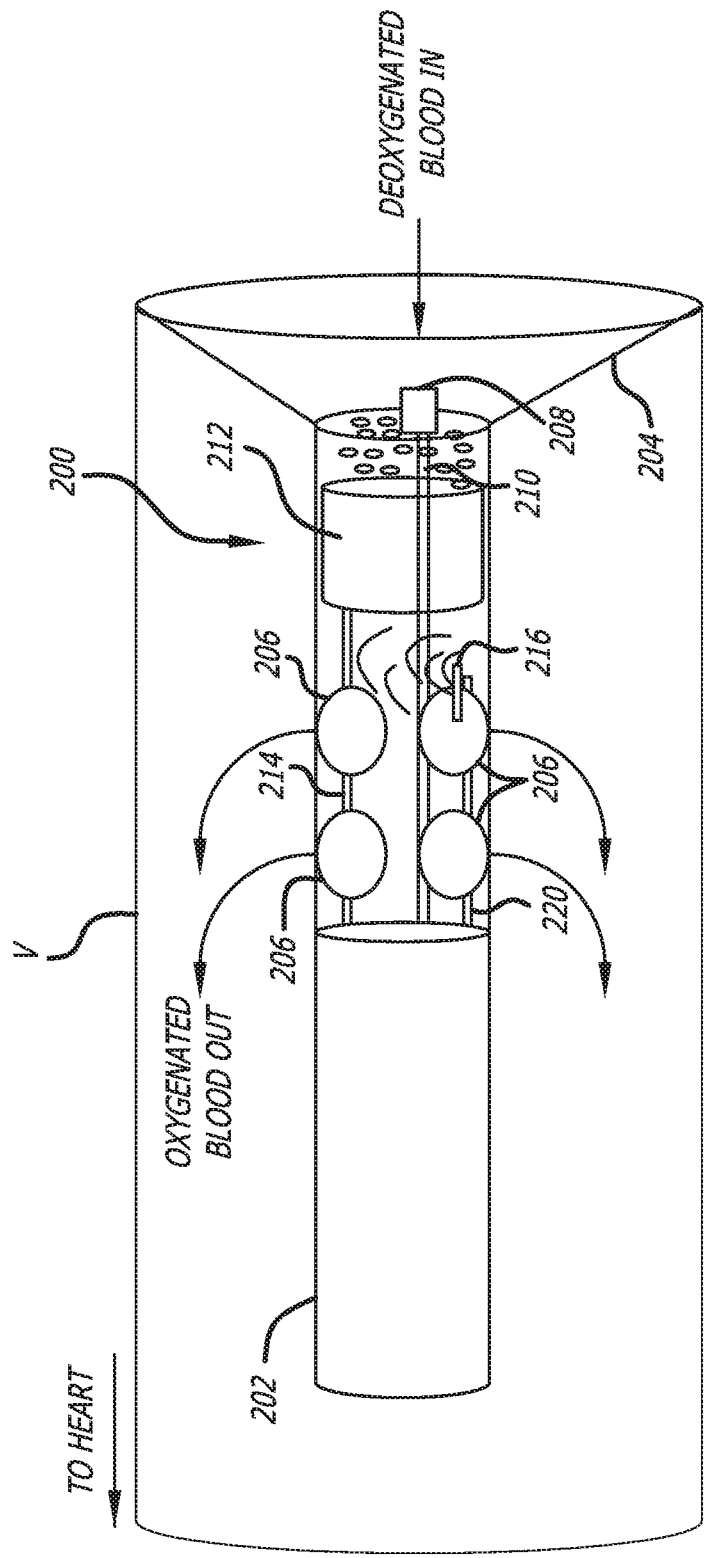
FIG. 11 is an elevation view of the embodiment of FIG. 10 with the vein removed to show detail.

Turning now to FIGS. 10-13, there is shown a continuous infusion embodiment 200 of an oxygenation device of the invention. This embodiment uses the patient's blood as the medium into which the oxygen is infused and ensonified. FIG. 10 shows the distal end of the device within a vein V of the patient to illustrate that the catheter is smaller than the vein, allowing room for the outflow of oxygenated blood from the sidewalls of the catheter. FIG. 11 shows the distal end of the device 200 without the vein to show the details of the device.

The device 200 includes a catheter 202 with a collapsible funnel 204 at one end that directs blood into the catheter 200. The catheter 202 has blood outflow holes 206 that allow the oxygenated blood to escape through the sidewalls of the catheter 202.

Within the catheter 202 is an oxygen infuser 208 connected to an oxygen inflow tube 210. Also within the catheter is an impeller pump 212 powered via pump power conductors 214. There is also a piezoelectric disc 216 powered by piezo power conductors 220.

Once the distal end of the device 200 is placed within the vein V of a patient, the funnel 204 expands to direct blood into the device 200. To prevent expansion prior to the target site, the funnel may be constrained by an outer sheath over the catheter 202 or other methods. The funnel 204 is constructed of a spring material, such as nitinol When the catheter is placed in the proper position, the outer sheath is pulled back and the funnel is expressed. Alternatively, the intake funnel could be formed by a variety of other methods, such as a cylindrical woven nitinol mesh that shortens and widens when on or more pull wires attached to the distal end are pulled. The mesh can be located around the end of the catheter, where the proximal end is fixed to the catheter. Alternatively, the mesh can be attached to a wire or catheter within the catheter used to infuse and pump the nanobubbles. In such case, the wire mesh is pushed out of the catheter and the pull wire or catheter is pulled to enlarge the funnel 204.

The infuser 208 adds oxygen bubbles to the blood stream at the proximal end of the funnel 204. The infuser 208 is a (diffuser apparatus) with an inflow port for gas and an outflow surface with very small pores. A chamber with small pores (such as 1000-100 nm diameter pores) can be continuously charged with oxygen under pressure such that the pores emit small bubbles. A hydrophobic surface on the emitter pores of the diffuser can be used to improve creation of small bubbles.

The bubbles are less than 1 mm in diameter at this point. The bubbles and blood mixture enter the impeller pump 212, which provides a means to distribute the bubbles evenly throughout the mixture and create a non-linear flow of the blood/O2 mixture to maintain homogenous dispersion during the creation of nanobubbles. The pump sucks in the bubble oxygenated blood into the pump, causing a flow of blood past the infuser into the pump. An impeller pump, for example, will cause blood to flow across the infuser and into the impeller blades. The mechanical agitation of the impeller will also break up larger air bubbles into small bubbles. An inlet funnel with the infuser positioned within or immediately adjacent to funnel, ensures that gas-infused blood remains contained and that no large bubbles escape into the circulation.

In another embodiment, the pump is not employed. Instead, long and thin tentacle-like hollow biocompatible tubules made of poly-methylpentynol and other similar material that have micro-pores on their surface and the whole length in various distances and space between them, are placed intravenously and connected to a positive pressure oxygen supply. In that way nanobubbles are produces directly and continuously in the venous blood with flow rates of 0.1-10 ml/sec of 100% oxygen or other gasses. Alternatively, the hollow tubules are covered with surface sealants of various hydrophilic/phobic coatings that optimize the micro/nano bubble formation. Alternatively, the tentacle like tubules are combined with a sonification source as mentioned above.

Figure 12:
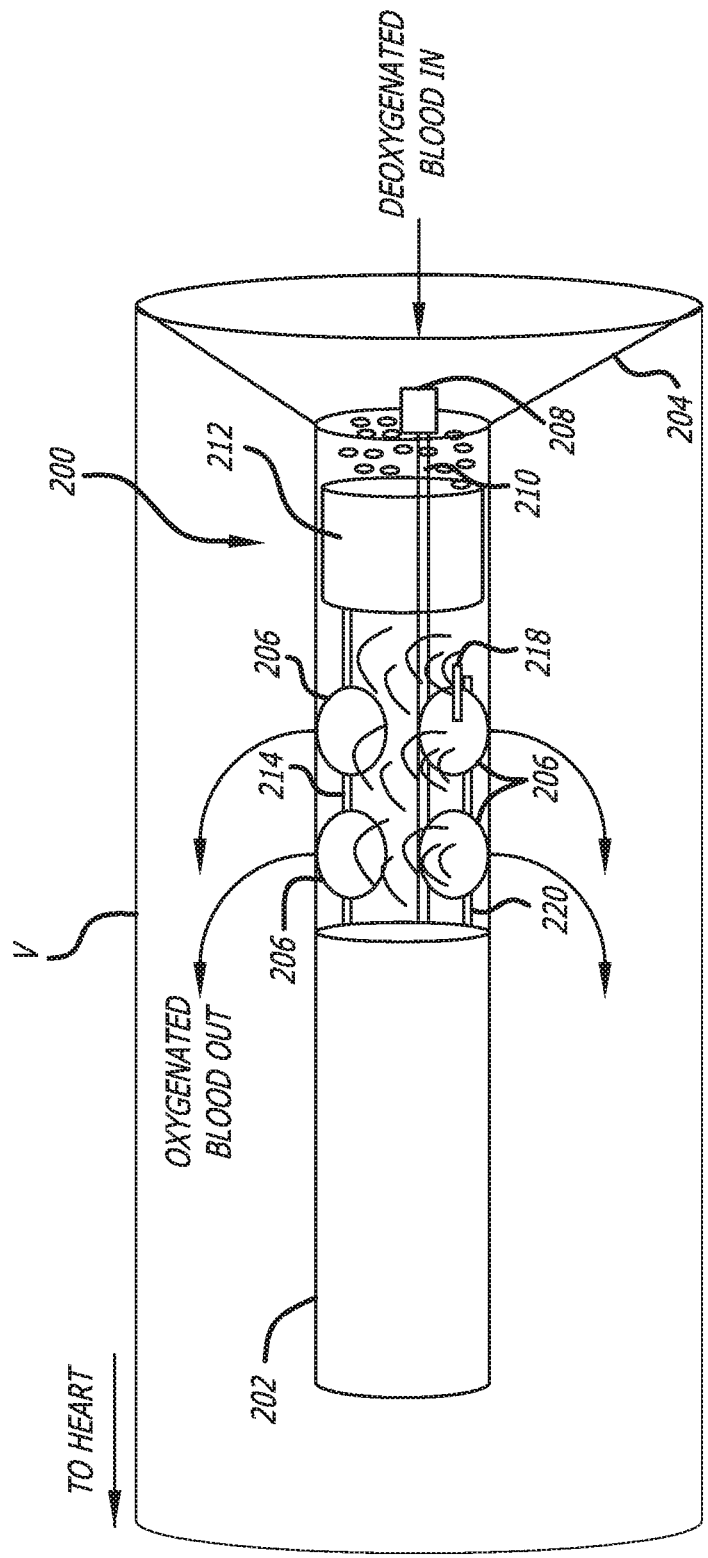
FIG. 12 is an elevation view of an embodiment using an ultrasonic wire instead of a disc.

The mixture then passes over an energized piezoelectric disc which breaks the bubbles up into nanobubbles. In one iteration, the outflow of the pump is propelled into a chamber attached to the pump on one end and open on the other end or on the side(s). Piezoelectric crystals in the funnel create ultrasound vibration (for example at 22-67 kHz), insuring that any larger air bubbles are reduced to <1000 nanometer (<1 μm) diameters. Alternatively, or in addition, piezoelectric crystals can be located on or around the pump apparatus or the inflow funnel to ensonify the blood as it travels into the funnel or through the pump. Alternatively, the ultrasonic energy can be emitted by a carrier, such as a metallic wire, that transmits the ultrasound energy from a source outside the body or a position inside the body that is distant from the blood flow being ensonified. FIG. 12 shows an ultrasonic transmission wire 218 being used instead of a disc 216. The newly oxygenated blood then passes through the blood outflow holes 206 and back into circulation to the heart.

Figure 13:
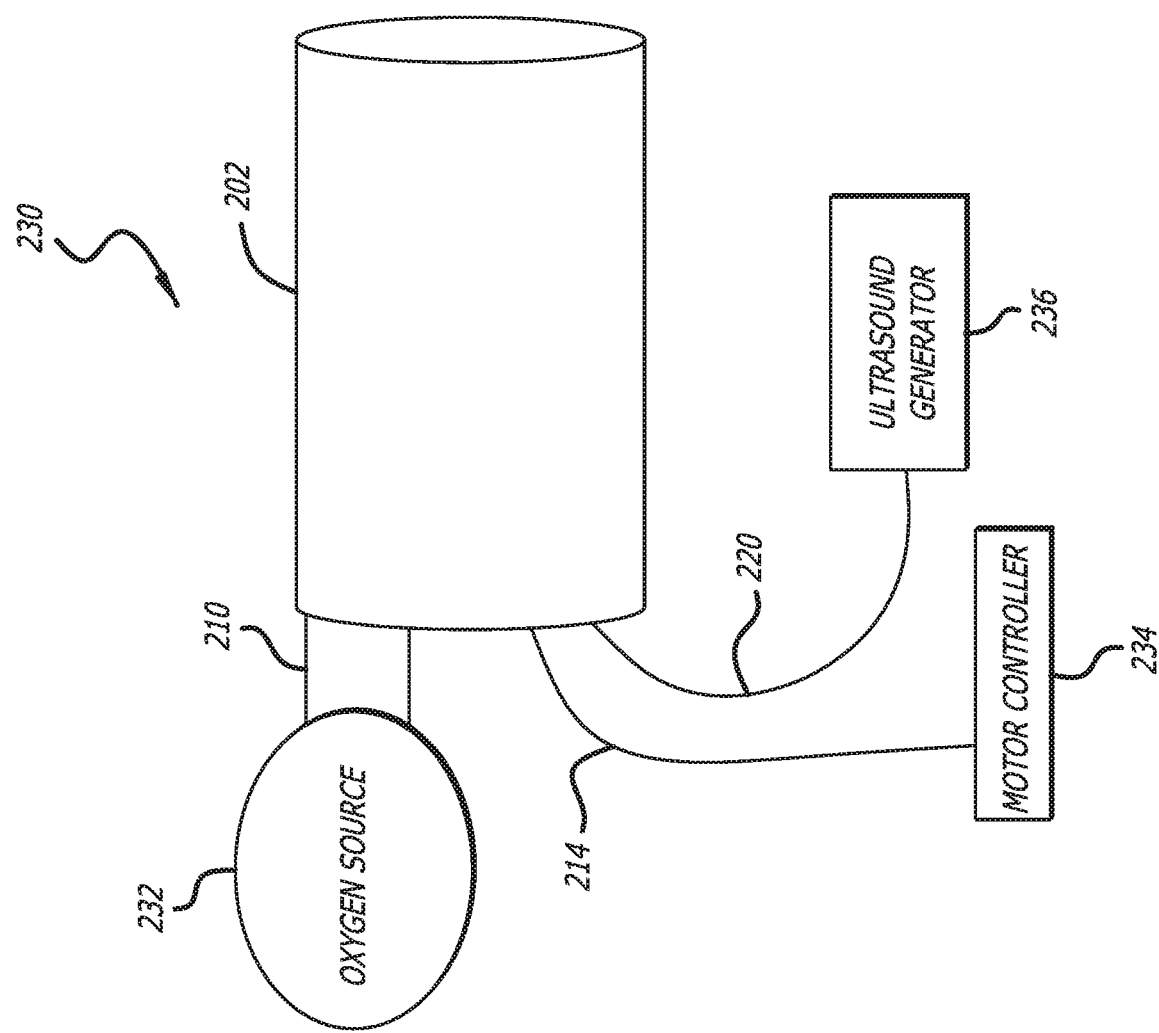
FIG. 13 is a schematic of a proximal end of the embodiment of an oxygen infusion catheter system of the invention.

FIG. 13 shows an embodiment 230 of a proximal end of the device 200. It can be seen an oxygen source 232 is connected to the proximal end of the oxygen inflow tube 210, which then enters into the proximal end of the catheter 202. There is also a motor controller 234 connected to the pump power conductors 214, and an ultrasound generator 236 attached to the piezo power conductors 220.

Figure 14:
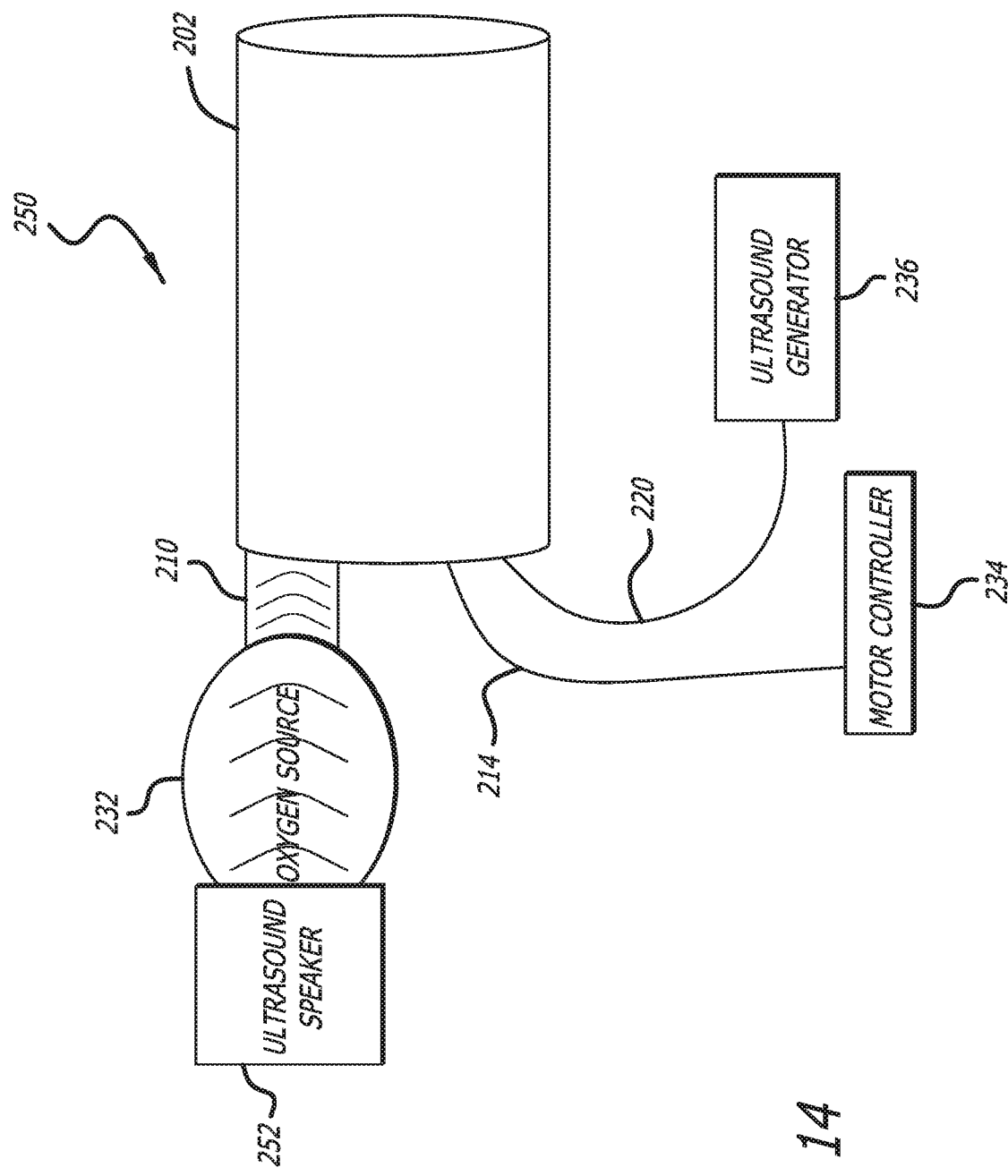
FIG. 14 is a schematic of a proximal end of the embodiment of an oxygen infusion catheter system of the invention; and, FIG. 15 is a schematic of a CO2 removal system of the invention.

FIG. 14 shows an embodiment 250 of a proximal end of the device 200. This embodiment 250 has an ultrasound speaker 252, or other pulsating mechanism, that creates pressure pulses of the incoming gas so that the emission of gas bubbles occurs in pulses that limit the volume of bubble emitted with each pulse. An additional embodiment employs vibration of the emitting chamber, which has the effect of facilitating formation of small bubbles by causing them to break free of the surface of the emitter after a small gas bubble has formed on the outer surface. In another embodiment, a rotating member on the inside or outside of the emitting chamber mechanically terminated bubble formation and frees the bubble from the surface. It is recognized that a combination of these methods can improve the emission of small gas bubbles.

Other Gases

Heretofore the infusion of oxygen has been discussed. However, the present invention could be used to infuse gases other than oxygen.

Nitic Oxide

In an additional embodiment, the problem of device-induced thrombosis is prevented by the administration of small concentration of nitric oxide gas (NO). NO has significant antithrombotic properties because it inhibits platelet activation. NO rapidly reacts with oxygen and has an in-vivo half life of about 7 seconds. As a result, it is an ideal agent to prevent device thrombosis because it provides local anticoagulation with minimal or no systemic effects. The problem is that the NO must be introduced separately from the oxygen. Therefore, a second NO carrying tube is placed in or around the catheter and the infusion occurs via a second infuser or adjacent to the blood flow steam through the device.

Nitric Oxide gas micro-nano bubble infusion can also be used for direct therapeutic interventions that do not require oxygen supplementation such, pulmonary hypertensions crisis, acute cardiogenic shock.

Inhaled Anesthetics

Using the above-mentioned embodiments inhaled anesthetics such as isoflurane, sevoflurane etc. can be infused in the form of micro/nano bubbles directly in the blood stream to provide anesthesia and post ischemic cardio and cerebral protection.

Extracorporeal System for Infusion of Nano-Bubbles into the Blood

It is recognized that the same general method described above could be performed outside the body, where a blood from a cannula in the venous system is pulled out of the body by a pump, infused with gas (e.g. oxygen or a combination of gases), the liquid-gas mixture is ensonified to create nanometer size gas bubbles, and the gas enriched blood is returned to the body, wither through an venous or arterial cannula.

One advantage of an extracorporeal method is that it can be combined with the method for removing $CO_2$ from the blood (described below) and a chamber for removal of any macroscopic air can be added. The chamber for removing macroscopic air consists of a chamber with an inflow and outflow port. The chamber is large enough to slow the velocity of blood flow in the system and allow time for macroscopic air to rise to the surface. The top of the closed chamber is then allowed to vent through a tube or opening at or near the top of the chamber. Negative pressure at the vent port facilitates air removal and a sensor of the effluent from the vent port that senses air can be used to control the negative pressure at the port. When no air is sensed, the negative is reduced (that is, the pressure is less negative).

An extracorporeal location also facilitates the use of a variety of sensors that can be added to feedback loops to control the pump, gas flow, and ensonification duration or intensity.

Apparatus and Method for Removing $CO_2$ from Blood Using Negative Pressure-Assisted Diffusion One aspect of the invention is an apparatus and method removing $CO_2$ from venous blood using a negative pressure-assisted diffusion through a permeable membrane. It is anticipated that this method will be used in conjunction with the method for oxygenating venous blood by direct generation of nanobubbles into venous blood.

One problem with simple oxygenation is that the $CO_2$ concentration in the blood will continue to build up in patients who do not have adequate lung respiration to eliminate the $CO_2$ generated by metabolic activity.

Blood oxygenators that also withdraw $CO_2$ from the blood have been described, but they require a large diffusion area consisting of hundreds or thousands of small tubes through which air is pumped under positive pressure and blood comes in contact with the outer part of the tubes in order to have enough surface area to provide adequate gas exchange. In addition, the infusion of oxygen at the same point necessitates a positive airflow pressure to oxygenate the blood. This positive airflow pressure impedes elimination of $CO_2$ from the blood because it reduces the $CO_2$ diffusion gradient from the blood to the air. As a result, effective elimination of $CO_2$ from the blood requires that the blood be passed over a large surface area of a semipermeable membrane to diffuse off sufficient quantities of $CO_2$.

Figure 15:
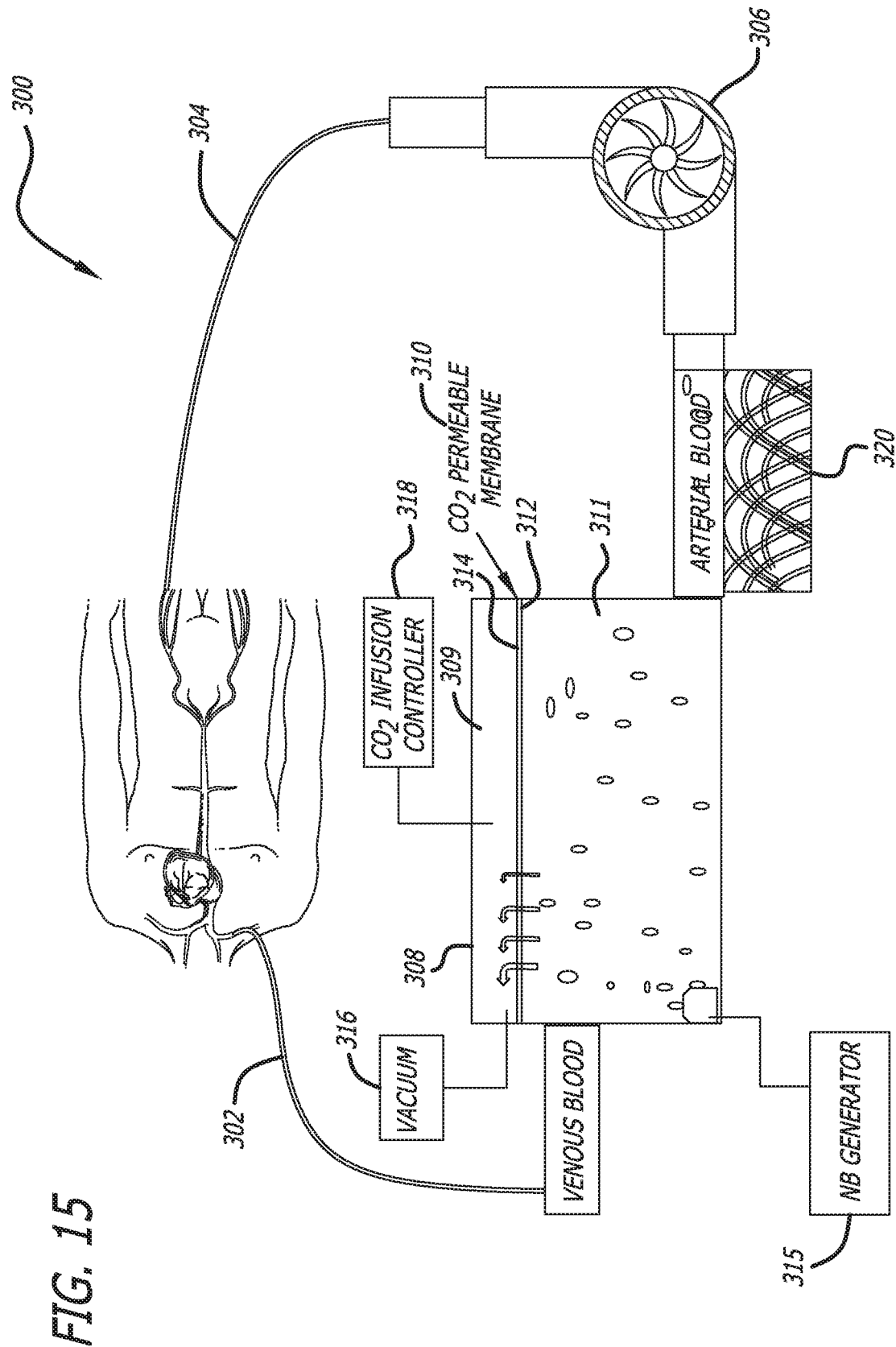

FIG. 15 shows an embodiment 300 of the invention that includes an apparatus and method for removing $CO_2$ from the blood. The embodiment 300 includes a tubing set 302 that is inserted or connected to the venous system (such as the vena cava) of an organism, another tubing set 304 that empties into the venous or arterial system, a pump 306 to transfer blood from the venous system between the two tubing systems 302 and 304, and a container 308 through which the blood flows. The container 308 is separated into two chambers, a first chamber 309 and a second chamber 311 by a membrane 310. The blood flowing through the second chamber 311 passes in contact with a membrane 310 permeable to dissolved $CO_2$. The membrane 310 has one surface 312 that is in contact with blood and another surface 314 that is exposed to the first chamber 309. The first chamber 309 may be filled with atmospheric air, other gas combinations (such as argon), or a fluid. The pressure in the chamber (relative to the blood on the other side of the membrane) can be varied using a pump 316 or other device that removes air or fluid from the chamber and by a valve 318 that controls the inflow of air or gas into the chamber. Typically, air in the chamber is held at a pressure less than the pressure in the tubing system, typically less than atmospheric pressure, in order to increase the diffusion gradient for $CO_2$. The blood $PCO_2$ can be modulated by variation of the vacuum and $CO_2$ partial pressure in the removal chamber side.

In this embodiment, blood $CO_2$ will be eliminated by diffusion through a permeable membrane attached to the blood flow circuit, such that one surface of the membrane in contact with the blood and the other side is in contact with the vented gas removal chamber. One or more membranes can be deployed in any configuration in order to increase the red blood cell transit times to optimize oxygenation, and $CO_2$ exchange.

Outside the membrane, a controlled gas and vacuum-capable environment will be used to control the level of $CO_2$ removal by either increasing or decreasing the $CO_2$ gradient to facilitate or retard the diffusion. Increasing the $PCO_2$ of this chamber would decrease the removal of blood $CO_2$ and vice versa. The vacuum would be deployed to enhance the $CO_2$ removal and decrease the need for a large diffusion surface. Additionally, in another embodiment, compounds that bind $CO_2$ (such as lime) are introduced in the gas chamber or placed in opposition to the gas flow to facilitate $CO_2$ binding, trapping the $CO_2$.

Combining the $CO_2$ removal system with an oxygenation system, such as 10 or 100, enhances the efficiency of $CO_2$ removal because the oxygen in the blood preferentially displaces $CO_2$ bound to hemoglobin. The oxygenation system is shown in FIG. 15 as 315, and is contained within the second chamber 311. The venous blood passes through the gas mixing chamber 311, where microbubbles oxygenate the blood to increase the $PvO_2$ from the typical ~40 mmHg to arterial levels of $PaO_2$ of 90-100 mmHg. At the point of oxygenation, the inbound (venous) blood's carboxy-hemoglobin will release $CO_2$ in favor of binding $O_2$. As a result, blood $PCO_2$ will rise. Infused oxygen increases plasma $CO_2$ and thereby increases $CO_2$ diffusion across the negative pressure assisted membrane. Conversely, nanometer diameter oxygen bubbles have a high surface tension and are resistant to diffusion across the membrane, reducing diffusion of oxygen contained in the blood. In addition, the oxygen nanobubbles provide ample oxygen supply to replaces any oxygen pulled out of the blood by negative pressure diffusion.

When combined with a system for blood oxygenation 315, the apparatus consists of a venous cannula and tubing that extends from the lumen of a vein on one end and to an arterial cannula that extends into the arterial system on the other end. Attached to tubing extending from the venous cannula is a gas-exchange chamber with active micro/nanobubble generation, a sonification chamber 320 to insure that the diffused gas consists of bubbles of <1000 nm diameter (as described above), and a blood flow generation pump 306 that pulls blood from the venous cannula and propels it towards the arterial cannula 304, where the blood may pass through one or more oxygenation chamber(s). The pump flow generation determines the blood transit times through the gas mixing and exchange chamber. With various combinations of chamber size and blood flow, oxygenation and blood $PCO_2$ levels can be further modulated to obtain the desired physiological outcome. In addition, based on the level of flow generation and the return path of the oxygenated blood the machine can be used either as lung replacement alone or as lung and heart replacement method similar to current veno-venous and veno-arterial extracorporeal membrane oxygenation.

The tubing system may have ports for infusion and removal of blood samples and medication infusion and also may have oxygen and $CO_2$ sensors to detect the partial pressure or content of oxygen, carbon dioxide, or other substances in the blood flow path.

It is recognized that gas infusion could result in the generation of macrobubbles (>10 micron diameter) that, if delivered to the circulation of a mammal could result in blood flow obstruction at the macrovascular level. An additional bubble trap can be deployed before or after the blood flow-generating pump to vent any bubbles that have been burst at the liquid surface. In the extracorporeal circulation, a semipermeable membrane (such as a thin silicone compound) that is in contact with the blood flow and also is oriented with gravity, such that the membrane is substantially above the blood, so the macro bubbles will congregate at the membrane surface, provides a method to vent the gas. The composition of gas on the other side of the membrane (the non-blood side) is controlled by the inflow of a gas of the desired characteristics (such as argon gas that will facilitate the diffusion of nitrogen through the membrane) and pressure (such as a negative pressure to facilitates gas diffusion.

It is recognized that the withdrawal of air in the form of macrobubbles will be facilitated by ultrasonic ensonification at or around the membrane site and by simple mechanical agitation to provide energy sufficient to overcome the surface tension of the bubbles.

It is also recognized that the concentrations of specific gases or compounds in the blood can be controlled by sensing the concentration of the gas or compound in the venous blood entering the system and then modulating by a feedback loop the inflow gas composition, the pressure of the gas in the evaporation chamber, the membrane area exposed for diffusion and other factors that affect diffusion of compounds across the diffusion membrane such as the transit time of the venous blood through the gas exchange chamber and removal membrane or membranes. In addition, sensors near or on the membrane or near the arterial inflow cannula can be used to provide feedback to the parameters affecting diffusion. For example, $PaCO_2$ levels can be adjusted to correct for metabolic and respiratory acidosis/alkalosis detected in either the inflow or outflow cannulas. The concentration of anesthetic gases can be controlled by detection of the concentration in either the inflow or outflow cannulas and adjustment of the anesthetic gas flow into the diffusion apparatus. A similar feedback loop can be employed where the concentration or $PO_2$ of oxygen is sensed in the system and used to alter the flow of oxygen into the diffuser and the power of the ultrasound used to ensonify the blood.

In another embodiment, additional gasses (in addition or separately from oxygen) can be infused as micro/nanobubbles in the gas/blood mixing chamber for therapeutic reasons such as NO, anesthetics or inert gases (e.g. xenon, argon) for post conditioning and or preconditioning effects.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of infusing blood with a gas comprising:
creating, in vivo, bubbles of gas in blood of a patient when that blood is contained within a catheter;
reducing said bubbles to nanobubbles within the catheter, said nanobubbles having diameters of less than 500 nm;
introducing the blood of the patient containing said nanobubbles into a bloodstream of the patient; and,
rupturing said nanobubbles using external energy at a target location.

2. The method of claim 1 wherein creating, in vivo, bubbles of gas in blood comprises creating bubbles of oxygen.

3. The method of claim 1 wherein rupturing said nanobubbles comprises energizing said nanobubbles using ultrasonic energy at a resonant frequency of said nanobubbles.

4. The method of claim 1 wherein reducing said bubbles to nanobubbles comprises ensonifying said bubbles.

5. The method of claim 1 wherein creating bubbles of gas in blood of the patient contained within the catheter includes first routing the blood, from the bloodstream of the patient, into the catheter.

6. The method of claim 5 wherein introducing the blood of the patient into the bloodstream of the patient comprises releasing the blood contained within the catheter back into the bloodstream of the patient through blood outflow holes created in the catheter.

7. A system for infusing blood with a gas comprising:
a gas source;
a liquid medium comprising blood;
a gas infuser connected to said gas source and located in said liquid medium that creates gas bubbles when gas from said gas source flows through said gas infuser;
an ensonifier located in said liquid medium and connected to a power source wherein when energized said ensonifier reduces said gas bubbles to nanobubbles, said nanobubbles having a diameter of less than 500 nm; and,
a catheter useable to deliver said nanobubbles in said liquid medium to a bloodstream of a patient from a portion of the catheter sized and shaped for in vivo placement within a blood vessel of the patient, wherein the portion includes the gas infuser and the ensonifier, and wherein the portion is defined by an opening in the catheter that receives blood from the bloodstream and an opening in the catheter that directs blood into the bloodstream.

8. The system of claim 7 wherein said gas source comprises an oxygen source.

9. The system of claim 7 wherein said gas infuser comprises a ceramic stone.

10. The system of claim 7 wherein said ensonifier comprises a piezoelectric ultrasound transducer.

11. The system of claim 7 wherein said ensonifier comprises an ultrasound generator attached to a wire.

* * * * *